(12) United States Patent
Wan et al.

(10) Patent No.: US 7,989,228 B2
(45) Date of Patent: Aug. 2, 2011

(54) METHOD AND STRUCTURE FOR SAMPLE PREPARATION FOR SCANNING ELECTRON MICROSCOPES IN INTEGRATED CIRCUIT MANUFACTURING

(75) Inventors: Xudong Wan, Shanghai (CN); Liqi Guo, Shanghai (CN); Eugene Wang, Shanghai (CN)

(73) Assignee: Semiconductor Manufacturing International (Shanghai) Corporation, Shanghai (CN)

( * ) Notice: Subject to any disclaimer, the term of this patent is extended or adjusted under 35 U.S.C. 154(b) by 348 days.

(21) Appl. No.: 11/378,888

(22) Filed: Mar. 16, 2006

(65) Prior Publication Data

US 2007/0111518 A1    May 17, 2007

(30) Foreign Application Priority Data

Nov. 17, 2005 (CN) .......................... 2005 1 0110573

(51) Int. Cl.
*H01L 21/66* (2006.01)
(52) U.S. Cl. .................... 438/14; 356/243.1; 356/243.4; 257/E23.179
(58) Field of Classification Search .................... 438/14; 257/E21.179; 356/243.1, 243.4
See application file for complete search history.

(56) References Cited

U.S. PATENT DOCUMENTS

| | | | | |
|---|---|---|---|---|
| 5,332,685 A * | 7/1994 | Park et al. | ...................... | 438/107 |
| 5,429,988 A * | 7/1995 | Huang et al. | .................. | 438/587 |
| 5,811,331 A * | 9/1998 | Ying et al. | ..................... | 438/253 |
| 6,358,860 B1 | 3/2002 | Scheer et al. | | |
| 6,583,000 B1 * | 6/2003 | Hsu et al. | ........................ | 438/222 |
| 6,861,118 B2 | 3/2005 | Kobayashi et al. | | |
| 6,911,372 B2 * | 6/2005 | Son | ............................. | 438/397 |
| 2005/0170603 A1 * | 8/2005 | Lee et al. | ....................... | 438/397 |

OTHER PUBLICATIONS

Office Action of Chinese Application No. 200510110573.0, dated Nov. 16, 2007 7 pages total (English translation not included).

* cited by examiner

*Primary Examiner* — Asok K Sarkar
*Assistant Examiner* — Julia Slutsker
(74) *Attorney, Agent, or Firm* — Kilpatrick Townsend and Stockton LLP (57) ABSTRACT

A method for using a calibration standard. The method includes providing a calibration standard. In a specific embodiment, the calibration standard has a substrate, a thickness of material having an edge region; and a conformal material of uniform thickness disposed on the edge region. The standard also has an upper surface pattern having the uniform thickness provided on the edge region. The method also includes using the upper surface pattern for a calibration process on a scanning electron microscope process.

9 Claims, 6 Drawing Sheets

METHOD AND STRUCTURE FOR SAMPLE PREPARATION FOR SCANNING ELECTRON MICROSCOPES IN INTEGRATED CIRCUIT MANUFACTURING

CROSS-REFERENCES TO RELATED APPLICATIONS

This application claims priority to Chinese Application No. 200510110573.0; filed on Nov. 17, 2005; commonly assigned, and of which is hereby incorporated by reference for all purposes.

BACKGROUND OF THE INVENTION

The present invention is directed to integrated circuits and their processing for the manufacture of semiconductor devices. More particularly, the invention provides a method and device for preparing a sample for imaging using a scanning electron microscope for analysis in the manufacture of integrated circuit devices, but it would be recognized that the invention has a much broader range of applicability.

Integrated circuits have evolved from a handful of interconnected devices fabricated on a single chip of silicon to millions of devices. Conventional integrated circuits provide performance and complexity far beyond what was originally imagined. In order to achieve improvements in complexity and circuit density (i.e., the number of devices capable of being packed onto a given chip area), the size of the smallest device feature, also known as the device "geometry", has become smaller with each generation of integrated circuits.

Increasing circuit density has not only improved the complexity and performance of integrated circuits but has also provided lower cost parts to the consumer. An integrated circuit or chip fabrication facility can cost hundreds of millions, or even billions, of U.S. dollars. Each fabrication facility will have a certain throughput of wafers, and each wafer will have a certain number of integrated circuits on it. Therefore, by making the individual devices of an integrated circuit smaller, more devices may be fabricated on each wafer, thus increasing the output of the fabrication facility. Making devices smaller is very challenging, as each process used in integrated fabrication has a limit. That is to say, a given process typically only works down to a certain feature size, and then either the process or the device layout needs to be changed. Additionally, as devices require faster and faster designs, process limitations exist with certain conventional processes and materials. Furthermore, testing techniques for failure analysis and other purposes are also limited with smaller and smaller design rules.

An example of a process that has limitations based upon a given feature size is a calibration process commonly used with scanning electron microscopes, commonly called SEMs. The conventional calibration process often relies upon calibration standards, which are provided by vendors of these scanning electron microscopes. Unfortunately, these standards have limitations. That is, such standards often have errors that range in size to about 6 nanometers or more, depending upon the technique used to manufacture the standards. These and other limitations of the conventional calibration standards can be found throughout the present specification and more particularly below.

From the above, it is seen that an improved technique for processing semiconductor devices is desired.

BRIEF SUMMARY OF THE INVENTION

According to the present invention, techniques for processing integrated circuits for the manufacture of semiconductor devices are provided. More particularly, the invention provides a method and device for preparing a sample for imaging using a scanning electron microscope for analysis in the manufacture of integrated circuit devices, but it would be recognized that the invention has a much broader range of applicability.

In a specific embodiment, the present invention provides a method for manufacturing an integrated circuit device, e.g., memory, ASIC, microprocessor, system on a chip. The method includes forming a calibration standard for a SEM process, e.g., CD SEM. The method for forming the calibration standard, which will be used to calibrate a scanning electron microscope for manufacture of integrated circuits. The method includes providing a substrate (e.g., silicon) including a surface region, which has a predetermined planarity. The method includes forming a thickness of material overlying the surface region. The thickness of material has a thickness surface region. The method includes forming a recessed region having a first depth within a portion of the thickness of material. The recessed region includes a bottom portion and an edge region.

In a preferred embodiment, the method forms a conformal layer of a uniform thickness overlying the thickness of material, the recessed region, bottom portion, and edge region. The method also fills a portion of the first depth such that a conformal layer surface is below the thickness surface region to cause the recessed region to have a second depth from the thickness surface region to the conformal layer surface region. The method fills an entirety of the recessed region to the second depth with a fill material to form a resulting surface region. The method planarizes the resulting surface region to form a pattern having the uniform thickness by exposing the thickness surface region. The method selectively removes a portion of the thickness of material and a portion of the fill material to form an elevated pattern structure from the pattern having the uniform thickness. In a specific embodiment, the elevated pattern has a height above a surface region of the thickness of material.

In an alternative specific embodiment, the present invention provides a method for using a calibration standard. The method includes providing a calibration standard. In a specific embodiment, the calibration standard has a substrate, a thickness of material having an edge region; and a conformal material of uniform thickness disposed on the edge region. The standard also has an upper surface pattern having the uniform thickness provided on the edge region. The method also includes using the upper surface pattern for a calibration process on a scanning electron microscope process.

Many benefits are achieved by way of the present invention over conventional techniques. For example, the present technique provides an easy to use process that relies upon conventional technology. Additionally, the method provides a process that is compatible with conventional process technology without substantial modifications to conventional equipment and processes. Preferably, the invention provides a calibration standard, which can be used to calibrate a critical dimension having a variance of one nanometer and less according to a specific embodiment. Depending upon the embodiment, one or more of these benefits may be achieved. These and other benefits will be described in more throughout the present specification and more particularly below.

Various additional objects, features and advantages of the present invention can be more fully appreciated with reference to the detailed description and accompanying drawings that follow.

DETAILED DESCRIPTION OF THE INVENTION

According to the present invention, techniques for processing integrated circuits for the manufacture of semiconductor devices are provided. More particularly, the invention provides a method and device for preparing a sample for imaging using a scanning electron microscope for analysis in the manufacture of integrated circuit devices, but it would be recognized that the invention has a much broader range of applicability.

As background, we will briefly provide an overview of scanning electron microscope analysis. CD SEM is an equipment used in semiconductor manufacturing environment to measure pattern size (CD) of patterns printed on silicon wafers. CDSEM is calibrated and matched to each other with certain standard sample. Two problems usually encountered include: (1) CD non-uniformity across the measurement line, where the measurement bar has huge variations due to lithographic process (e.g., resist profile, proximity effect and exposure beam interaction). Such variation will cause CDSEM calibration standard to yield inconsistent reading when measurement location is shifted along a CD bar. (2) When a sample is exposed under an electron beam during measurement, the electrons may charge the sample surface and change the image captured. As a result, the position of pattern edge will drift over time. Charging induced measurement drift makes matching of line/space measurement among CDSEMs across multiple tools in a fabrication facility difficult, introducing measurement uncertainty (drift and poor R&R).

There have been several ways to overcome the problem of sample charging: (1). Discharging electrons with a conductive material/substrate, so the charge will not build up on one spot; (2). Preparing enough samples with acceptable CD variation (using film thickness control instead of conventional CD width control) so that new sample can replace a charged and disqualified spot on one sample.

In semiconductor manufacturing, patterns are generated by microlithography and reactive ion etching. Due to limitation in optics resolution and material chemistry, it is difficult to shrink a pattern size. Moreover, CD variation of small patterns could be as high as 5 to 10 nanometers even in a small range of 10 microns. With the method described in this invention, the pattern CD is defined by a film thickness. The CD uniformity across a CD measurement bar is determined by the uniformity of film (e.g., a dielectric film) deposition. The typical thickness variation film thickness (e.g., a dielectric film) is 3% across an eight inch wafer. The film thickness uniformity in an area of 1 $cm^2$ (micro-scale range) can be as low as 0.3%, which corresponds to 0.4 nanometer CD variation for a 130 nanometer pattern. If a single measurement point has a 1,000 $micrometer^2$ area, there are about 100,000 samples in a chip of 1 $cm^2$. To validate the above invention and, a statistical test procedure is designed as follows:

Suppose for a specification process, the target value of the CDSEM is c, the variance of CDSEM is $\sigma^2$, (if $\sigma^2$ is unknown, we can take a sample of 30 to 50 points to estimate it, i.e. let sample standard deviation $s=\hat{\sigma}$). It is often required that the average value of a testing sample for CDSEM be between c−d and c+d. If the CDSEM is stable or under statistical control, then $$d = t_{\alpha/2, n-1} \frac{\sigma}{\sqrt{n}}$$

(when $\sigma$ is known) or $$d = t_{\alpha/2, n-1} \frac{s}{\sqrt{n}},$$

(when $\sigma$ is unknown), n is the size of the testing sample and $t_{\alpha/2, n-1}$ is a t-table value determined by a and n. A value of 0.05 is usually chosen for $\alpha$ for a 95% confidence level. From $$d = t_{\alpha/2, n-1} \frac{\sigma}{\sqrt{n}}, \text{ or } d = t_{\alpha/2, n-1} \frac{s}{\sqrt{n}},$$

the minimal testing sample size n can be calculated. Thus, from a testing sample of size n, if the average value of CDSEM is between c−d and c+d, then we have 95% (for $\alpha$=0.05) confidence to conclude that the above created CDSEM is stable and fit the specific process.

A method for operating a scanning electron microscope using a calibration standard according to an embodiment of the present invention can be outlines briefly as follows:

1. Provide a calibration standard, which has a substrate, a thickness of material having an edge region, a conformal material of uniform thickness disposed on the edge region, and an upper surface pattern having the uniform thickness provided on the edge region;
2. Insert the calibration standard into a scanning electron microscope;
3. Initiate operation of the scanning electron microscope;
4. Begin calibration process;
5. Use the upper surface pattern for a calibration process on a scanning electron microscope process;
6. Complete calibration process; and
7. Initiate operation of scanning electron microscope process using production devices;
8. Perform other steps, as desired.

The above sequence of steps is a method according to an embodiment of the present invention. As shown, the method provides a method for calibrating a scanning electron microscope process for semiconductor devices according to a specific embodiment of the present invention. Other alternatives can also be provided where steps are added, one or more steps are removed, or one or more steps are provided in a different sequence without departing from the scope of the claims herein. Further details of the present method can be found throughout the present specification and more particularly below.

Figure 1:
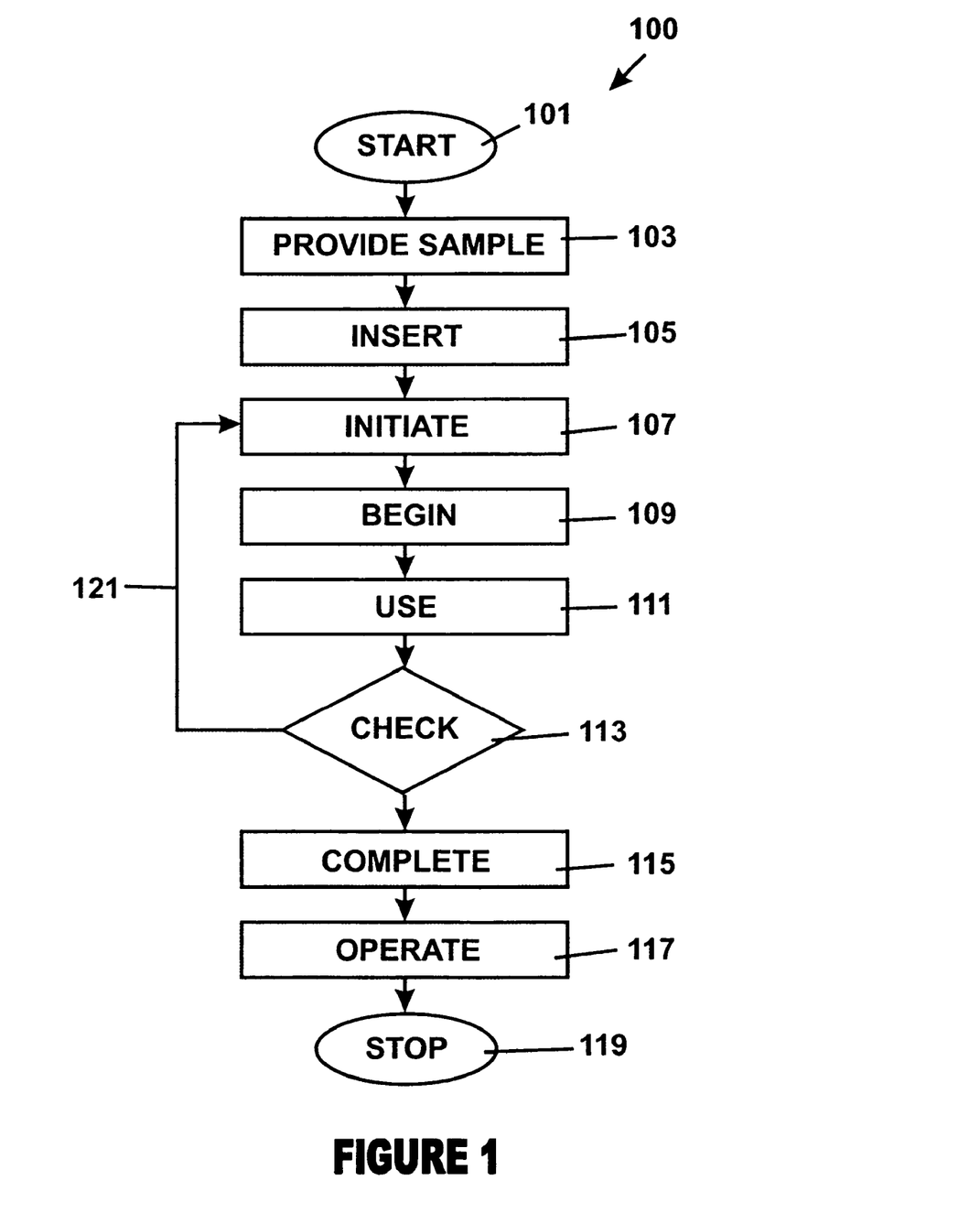
FIG. 1 is a simplified flow diagram of a method of using a calibration sample according to an embodiment of the present invention.

FIG. 1 is a simplified flow diagram 100 of a method of using a calibration sample according to an embodiment of the present invention. This diagram is merely an example, which should not unduly limit the scope of the claims herein. One of ordinary skill in the art would recognize other variations, modifications, and alternatives. As shown, the present invention provides a method for operating a scanning electron microscope using a calibration standard according to an embodiment of the present invention. As shown, the method begins with start, step 101. The method includes providing a calibration standard, which has a substrate, a thickness of material having an edge region, a conformal material of uniform thickness disposed on the edge region, and an upper surface pattern having the uniform thickness provided on the edge region. Further details of the calibration standard can be found throughout the present specification and more particularly below.

In a specific embodiment, the method includes inserting (step 105) the calibration standard into a scanning electron microscope. The method begins initiation (step 107) of operation of the scanning electron microscope. The method begins (step 109) the calibration process. In a specific embodiment, the method uses (step 111) the upper surface pattern for a calibration process on a scanning electron microscope process. In a preferred embodiment, the upper surface pattern is highly accurate. Depending upon the embodiment, the method checks (step 113) if the calibration process is desirable or undesirable. If undesirable, the method can return via branch 121 to step 107. Alternatively, the method completes (step 115) the calibration process.

In a specific embodiment, the method initiates (step 117) operation of scanning electron microscope process using production devices or other sample. The method continues to operating the scanning electron microscope process. The method then stops, step 119. Of course, there can be other variations, modifications, and alternatives.

The above sequence of steps provides a method according to an embodiment of the present invention. As shown, the method uses a combination of steps including a way of using a calibration sample in a scanning electron microscope process for the manufacture of integrated circuit devices. Other alternatives can also be provided where steps are added, one or more steps are removed, or one or more steps are provided in a different sequence without departing from the scope of the claims herein. Further details of the present method, including a way of fabricating the present calibration sample, can be found throughout the present specification and more particularly below.

Figure 2:
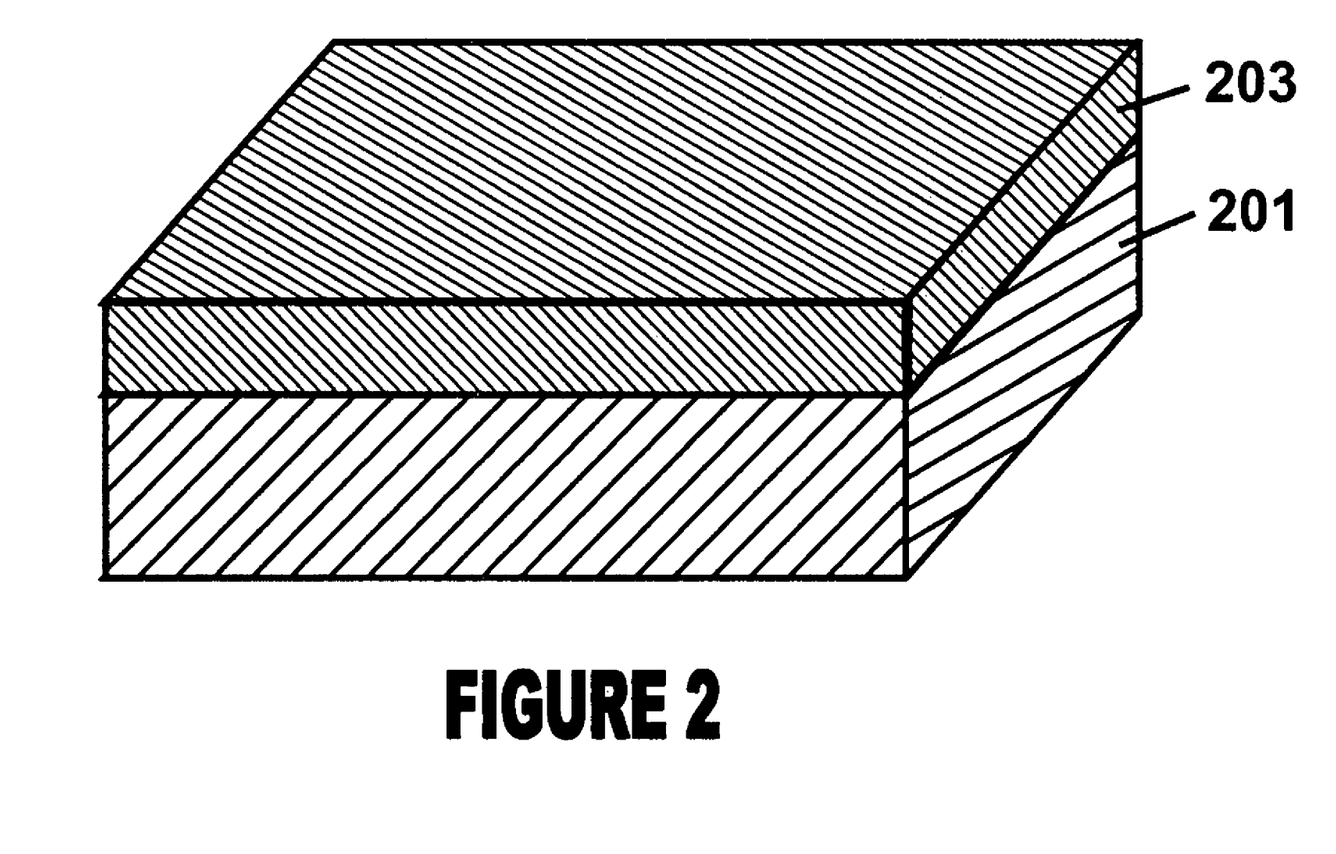
FIGS. 2 through 6 illustrate a method for fabricating a calibration sample according to an embodiment of the present invention.

FIGS. 2 through 6 illustrate a method for fabricating a calibration sample according to an embodiment of the present invention. These diagrams are merely examples, which should not unduly limit the scope of the claims herein. One of ordinary skill in the art would recognize other variations, modifications, and alternatives. As shown, the present invention includes a method for manufacturing an integrated circuit device, which has a method for forming a calibration standard for a SEM process. In a specific embodiment, the method for forming the calibration standard includes providing a substrate 201 including a surface region, which has a predetermined planarity. As shown in FIG. 2, the method includes forming a thickness of material 203 overlying the surface region. In a preferred embodiment, the thickness of material has a thickness surface region.

Figure 3:
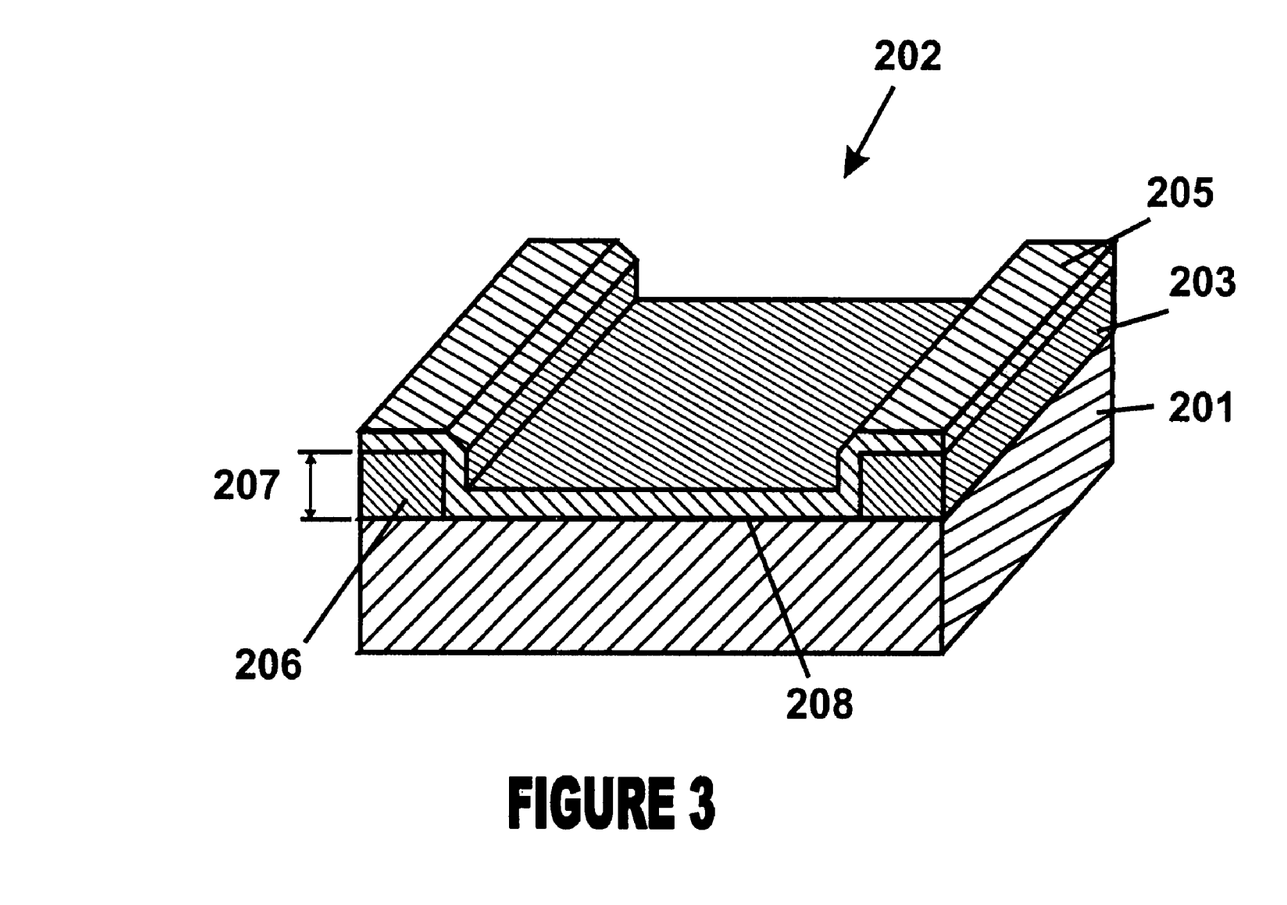

In a specific embodiment, the method includes forming a recessed region 202 having a first depth 207 within a portion of the thickness of material as shown in FIG. 3. In a specific embodiment, the recessed region includes a bottom portion and an edge region. The bottom portion 202 and the edge region 206 are shown. In a specific embodiment, the method includes forming a conformal layer 205 of a uniform thickness overlying the thickness of material including the recessed region, bottom portion, and edge region. The method also includes filling a portion of the first depth such that a conformal layer surface is below the thickness surface region to cause the recessed region to have a second depth from the thickness surface region to the conformal layer surface region according to a specific embodiment. In a specific embodiment, the fill material is polysilicon and/or other like material with desired thicknesses. Of course, there can be other variations, modifications, and alternatives.

Figure 4:
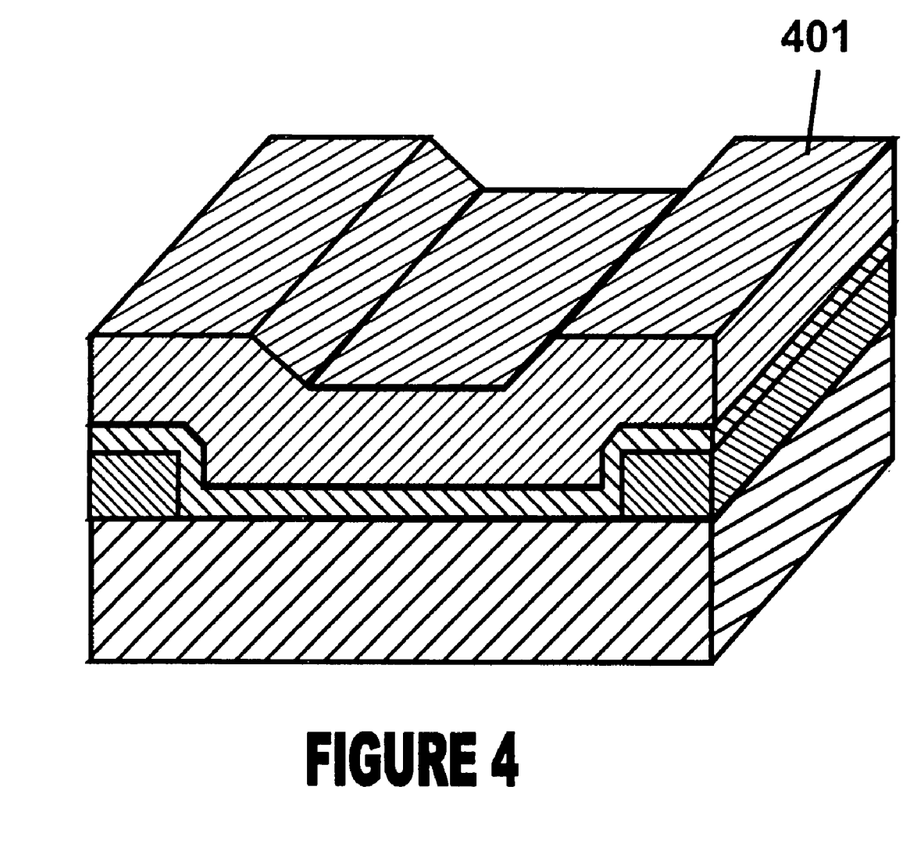
Figure 5:
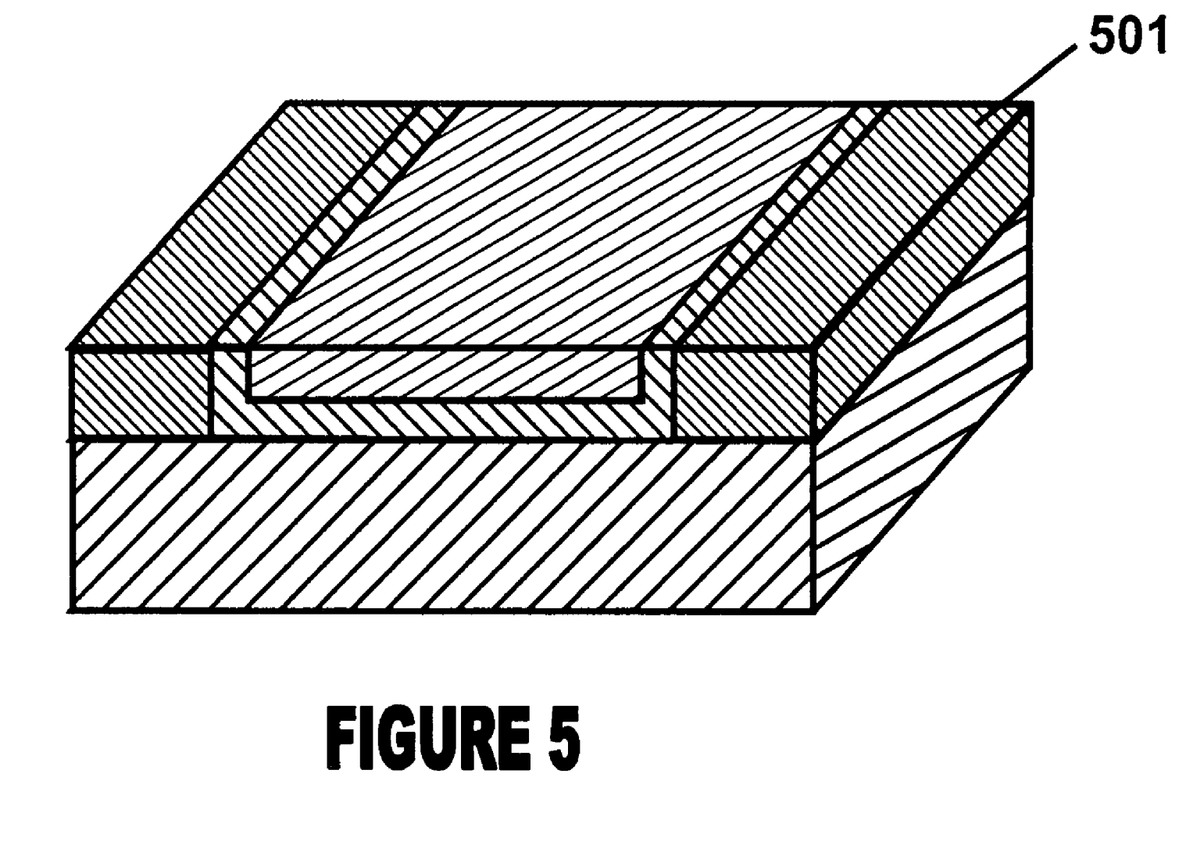
Figure 6:
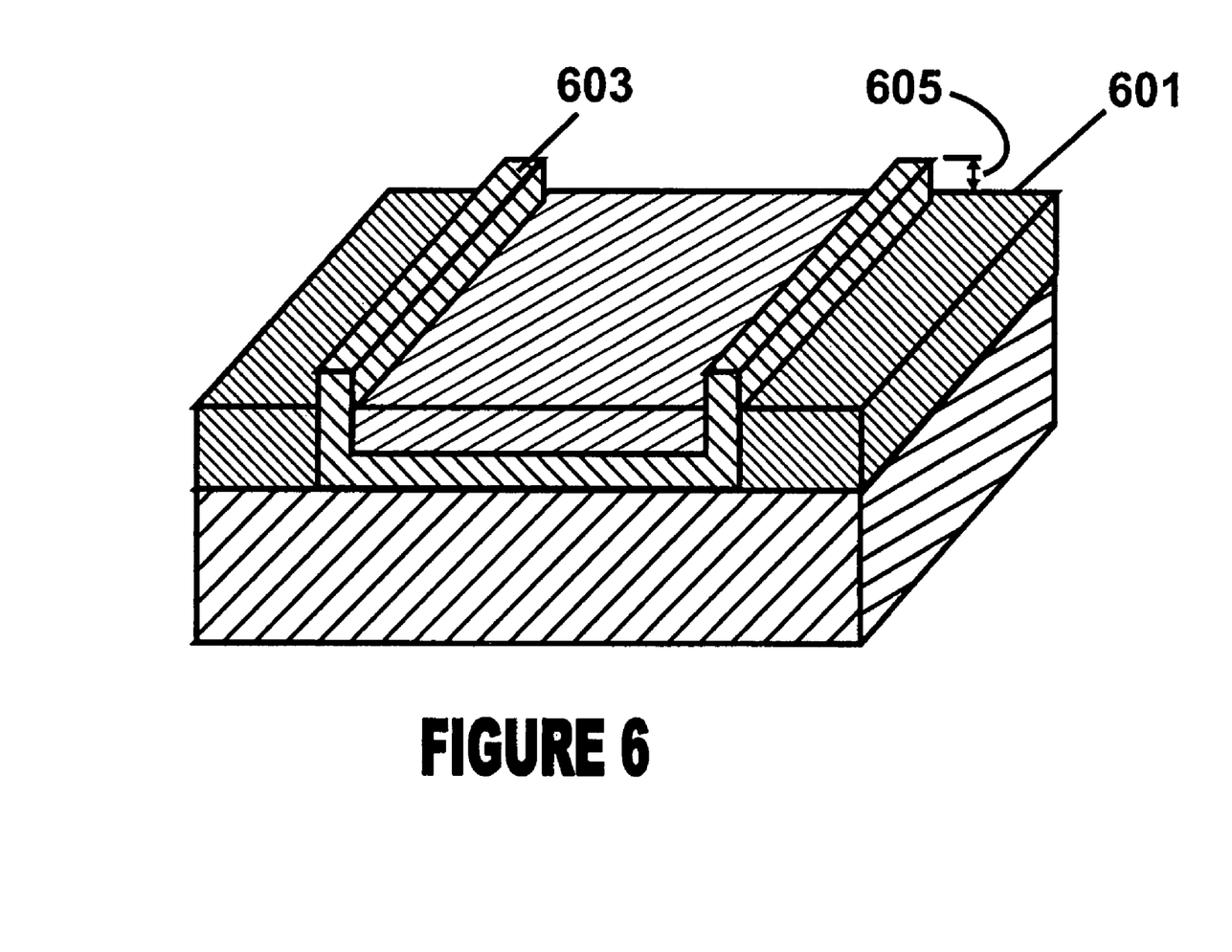

In a specific embodiment, the method includes filling an entirety of the recessed region to the second depth with a fill material 401 to form a resulting surface region as shown in FIG. 4. In a specific embodiment, the fill material is a dielectric material such as silicon dioxide, silicon nitride, any combination of these, and others. As shown in FIG. 5, the method includes planarizing the resulting surface region 501 to form a pattern having the uniform thickness (e.g., 300 Angstroms to about 1 micron) by exposing the thickness surface region. In a specific embodiment, the planarizing occurs using a chemical mechanical polishing process but can be others. In a specific embodiment, the method also includes selectively removing a portion of the thickness of material and a portion of the fill material to form an elevated pattern structure 603 from the pattern having the uniform thickness. In a preferred embodiment, the pattern varies no more than about 1 nanometer. In a preferred embodiment, the elevated pattern has a height 605 above a surface region 601 of the thickness of material. In a specific embodiment, the height is at least 100 Angstroms, but can be others. Of course, there can be other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for manufacturing an integrated circuit device comprising:
   providing a substrate including a surface region, the surface region having a predetermined planarity;
   forming a thickness of material overlying the surface region, the thickness of material having a thickness surface region;
   forming a recessed region having a first depth within a portion of the thickness of material, the recessed region including a bottom portion and an edge region, the bottom portion being an exposed portion of the surface region of the substrate;
   forming a conformal layer of a uniform thickness overlying the thickness of material including the recessed region, bottom portion, and edge region, and filling a portion of the first depth such that a conformal layer surface is formed below the thickness surface region to cause the recessed region to have a second depth from the thickness surface region to the conformal layer surface region, wherein the conformal layer comprises a polysilicon material;
   filling an entirety of the recessed region to the second depth from the thickness surface region to the conformal layer surface region with a dielectric fill material overlying the conformal layer to form a resulting surface region, wherein the dielectric fill material directly contacts the conformal layer including the conformal layer surface region formed below the thickness surface region;
   planarizing the resulting surface region to form a pattern using the conformal layer having the uniform thickness by exposing the thickness surface region and maintaining a portion of the dielectric fill material;
   selectively removing a portion of the thickness of material and a portion of the dielectric fill material to form an elevated pattern structure from the pattern having the uniform thickness, the elevated pattern having a height above a surface region of the thickness of material, while maintaining the conformal layer substantially intact;

calibrating a scanning electron microscope using the elevated pattern structure; and measuring a pattern size using the calibrated scanning electron microscope.

2. The method of claim 1 wherein the height is at least 100 Angstroms.

3. The method of claim 1 wherein the substrate is a semiconductor wafer.

4. The method of claim 1 wherein the uniform thickness varies by no more than 1 nanometer.

5. The method of claim 1 wherein the dielectric fill material is selected from a silicon nitride, a silicon oxide, or other dielectric material.

6. The method of claim 1 wherein the bottom portion exposes a portion of the substrate.

7. The method of claim 1 wherein the recessed region is formed by an etching process.

8. The method of claim 1 wherein the planarizing is a chemical mechanical polishing process.

9. The method of claim 1 wherein the pattern is a line having the uniform thickness.

* * * * *